United States Patent [19]

Ruiseco

[11] Patent Number: 4,849,214

[45] Date of Patent: Jul. 18, 1989

[54] OIL BASED SCALP TREATMENT COMPOSITION

[76] Inventor: Mario G. Ruiseco, 12 Running Brook La., Sterling, Va. 22170

[21] Appl. No.: 11,610

[22] Filed: Feb. 6, 1987

Related U.S. Application Data

[63] Continuation-in-part of Ser. No. 700,975, Feb. 12, 1985.

[51] Int. Cl.$^4$ .................. A61K 7/06; A61K 31/00; A61K 35/78; A61K 31/295
[52] U.S. Cl. ..................... 424/74; 424/195.1; 424/705; 424/714; 514/502; 514/692; 514/880
[58] Field of Search ............ 424/74, 165, 195.1; 514/880, 502, 692

[56] References Cited

U.S. PATENT DOCUMENTS

| | | | |
|---|---|---|---|
| 3,932,611 | 1/1976 | McCarthur | 424/70 |
| 4,358,286 | 11/1982 | Grollier et al. | 8/405 |
| 4,405,604 | 9/1983 | Sunley | 424/165 |
| 4,438,095 | 3/1984 | Grollier et al. | 424/70 |
| 4,505,902 | 3/1985 | Millard | 424/195.1 |

OTHER PUBLICATIONS

Chem. Abst. 99:191665x 1983.

*Primary Examiner*—John W. Rollins
*Attorney, Agent, or Firm*—Ronald R. Snider

[57] ABSTRACT

An oil based composition for the treatment of dry scalp conditions, dry skin conditions, and human hair is shown and decribed. This composition is made by placing grated avocado seed in a mineral oil solution for a period of time, straining the grated avocado seed from the mineral oil solution, and addition of other ingredients which include flowers of sulfur, castor oil, cod liver oil, peppermint spirit, orange water, spirit of camphor, and arnica.

The composition described herein is used to treat dry scalp and skin conditions by placing the mixture on the treatment area for a substantial period of time and then shampooing it off.

4 Claims, No Drawings

OIL BASED SCALP TREATMENT COMPOSITION

RELATED APPLICATION

This application is a continuation-in-part of U.S. application Ser. No. 700,975 filed Feb. 12, 1985, now abandoned.

I. Field of the Invention

This invention is a composition of oil based materials which is used for the treatment of dry skin and scalp conditions. The composition is used as a treatment prior to shampooing, or as a long-term treatment of scalp or skin where extremely dry conditions are encountered. This composition may be left upon a human scalp for as long as several days, and may be applied with the additional use of heat.

II. Description of the Prior Art

Prior Art cited in the parent application Ser. No. 700,975 includes U.S. Pat. Nos. 4,505,902 Millard, 3,932,611 McCarthur, Cosmetic Science and Technology, 1957 and Conn's Current Therapy P. 601, 1984.

U.S. Pat. No. 4,283,384, Jacquet et al., teaches the use of avocado oils for use in cosmetic compositions. This reference, however, teaches away from the use of an oil base and utilizes the oil as a component of a polymerized, unsaturated monomer.

U.S. Pat. No. 4,438,095, Grollier et al., teaches the use of avocado in combination with mineral oil or vegetable oil. This reference, however, does not utilize an oil based composition for the skin and instead uses an aqueous solution. The Grollier patent teaches that the use of a purely oil-based composition for the skin is not fully satisfactory because of problems with spreading and the resulting greasy appearance, as well as an unpleasant greasiness to the touch.

U.S. Pat. No. 4,366,099, Gaetani et al., discloses the use of avocado oil or other oils with a homopolymerizable and hydrophilic monomer in the presence of an initiator. By this process, the oils are modified and altered. The modification essentially constitutes polymerization of the oils.

U.S. Pat. Nos. 4,358,286, Grollier et al., and 4,460,488, Grollier et al., teach the use of arnica in cosmetic composition. However, these references teach away from the use of oils and other active ingredients. Both of these references, rather, teach that the active ingredients are to be removed prior to application or completion of the mixture.

U.S. Pat. No. 4,342,742, Sebag et al., discloses the use of sulphonamide and sulphoxide in combination with other materials to form a hair treatment composition.

U.S. Pat. No. 4,129,644, Kalopissis et al., discloses a cosmetic composition containing a superoxide dismutase.

SUMMARY OF THE INVENTION

This invention is a mixture of oils, avocado seed extracts, and arnica which forms a hair treatment composition. By this invention, extracts of avocado seed are obtained by grating avocado seeds and allowing the grated seed portions to remain in a mineral oil for at least two weeks, and preferably four weeks. The grated avocado seed is removed from the oil mixture by straining the seed portions from the oil. Additional oils, such as castor oil and cod liver oil, and other ingredients are added to the mixture of avocado and mineral oil. Arnica is then added to the oil solution to complete the mixture.

The composition in accordance with this invention may be applied to the human skin or scalp to relieve dry conditions. The composition in accordance with this invention may be applied to the hair and heated with a hair dryer in order to hasten the absorption of the composition into the scalp. This composition may also be used for long-term treatment of scalp conditions by applying the composition overnight, or for a period of up to one week.

It has been found that the composition of this invention restores oil to otherwise dry skin conditions and is effective in treatment of dandruff. This composition has also been found to be effective in treatment of dry skin conditions which result from certain medical procedures such as medication for heart patients, chemotherapy used in cancer treatment, and radiation used in cancer therapy.

DESCRIPTION OF THE PREFERRED EMBODIMENTS

The composition of this invention is an oil based material which includes several different oils, both vegetable and mineral, extracts from avocado seeds, and other ingredients. The vegetable oil may be a vegetable cooking oil as found in a food market. The mineral oil may be a motor oil as used for automobile machinery lubrication. Castor oil is also another readily available vegetable oil.

The composition of this invention may be produced by the following process.

Step 1: Grate four avocado seeds into small fragments and place the avocado seed fragments into 400 g of petroleum based oil. This mixture is placed in a room at room temperatures for a period of three to four weeks for aging. During the three to four week period, the petroleum oil takes up color from the avocado grated fragments, and thereby absorbs certain extracts from the avocado.

Step 2: Upon completion of the aging of the petroleum oil and avocado grated material, the grated material is strained from the petroleum oil. The straining process may be by the use of a cloth and a bowl. The cloth may be ordinary cheesecloth which is used in food preparation and canning. The straining removes the larger fragments of grated avocado and allows small fragments of avocado to pass through the strainer and into the bowl used for collecting the avocado and oil mixture. By this separation procedure, almost all of the mineral oil is separated from the avocado gratings.

Upon separation of the avocado and oil, approximately 400 g of oil and avocado extract is obtained.

Step 3: When new avocado seed gratings are used, it has been found that the used gratings may be once again placed in a quantity of oil (200 g instead of 400 g) so that additional avocado extract may be absorbed over another three to four week period.

Step 4: Additional ingredients are then added to the avocado oil mixture from Step 2 in accordance with the following proportions:
 a. 1 g of flowers of sulfur;
 b. 100 g of castor oil;
 c. 200 g of cod liver oil;
 d. 15 g of peppermint spirit;
 e. 50 g of orange water;
 f. 50 g of spirit of camphor;
 g. 500 g of tincture of arnica in liquid form which is 66% alcohol and 100 ml of the drug, as sold by Lilly NDC 0002-2563-58 Tincture No. 4.

Step 5: Once the above ingredients are added to the basic oil and avocado mixture, the composition is placed in a large container and is ready for immediate use. It has also been found that the alcohol from the ingredients aids in the mixing and blending of the composition of this invention. During use, it has been found necessary to shake the mixture very well prior to application. By the shaking step, the very fine avocado seed portions in the mixture are redisbursed in the basic oil material. Due to the tendency of the avocado seed remaining in the solution to settle out, it has been found that it is necessary to shake the solution each time before application.

The materials used to form this composition are commonly available items. The orange water is a preparation made by crushing orange peel and/or pulp and using water to rinse the crushed orange parts. The oil may be a light grade petroleum based motor oil such as an engine or motor oil. The castor oil and cod liver oil are both readily available from drug stores. The cod liver oil may be the type wherein vitamin A and vitamin D are used as supplements. The peppermint spirit is available at drug stores and is of the type used to treat mild stomach aches (Peoples Drug Store NDC 0426-0112-31). The spirits of camphor is commonly available in drug stores and is in an alcohol solution of 80 to 90 percent (Peoples Drug Store NDC 0426-0131-02).

The arnica is obtained as tincture arnica which is the type used for application to the skin for relief of pain from sprains and bruises. In the type used, the mixture is 66 percent alcohol and 100 ml of solution contains 20 g of arnica. Tincture arnica by Lilly NDC 0002-2563-58 Tincture No. 4 may be used.

The composition in accordance with this invention is typically used by placing the composition on the scalp by wetting cotton in the composition and placing on the person's head. Next, a plastic cap is placed over the head and heat from a hair dryer is applied for 5 to 10 minutes. The treatment is most effective when high heat is used. Next, the oil composition is rinsed out of the hair by shampooing twice. Then the hair is set in the conventional way by use of rollers and pins.

An alternative method of use is the placement of a cap over hair treated with the composition and leaving the composition on the hair overnight. This provides for a long period of time in which the beneficial effect of the mixture may be absorbed into the scalp and hair.

Treatment of dry skin conditions produced by radiation therapy given to cancer patients has been found to be effective when there is a continuous application of the composition for a period of up to 6 days. In this type of hair treatment, the composition is placed on the scalp by wetting cotton, and additional oil is added throughout the 6-day period. Oil is removed at the end of the treatment period by shampooing twice and setting the hair in the usual fashion. It has been found that this treatment of hair of cancer patients undergoing radiation treatment prevents the drying out of the hair and concurrent loss of oils which is otherwise produced by this type of cancer treatment therapy.

It has also been found that this composition is effective in preventing loss of hair which occurs as a result of treatment of certain heart patients. Heart patients having angina often experience loss of hair due to the medication. However, treatment by this composition as set forth above has been found to eliminate this side effect of the medication.

It has also been found that this composition is effective in treatment of other dry scalp conditions. Typical dandruff conditions resulting from dry scalp have been treated effectively with this composition.

This composition has been found to be effective in prevention of hair loss when the user is undergoing chemo therapy for cancer. It has been found that the hair grows back and has a natural shine.

In users who receive INDERAL it has been found that hair loss is prevented and that shine is maintained.

The benefits from this composition have been found to comprise reduction of scalp itch, thickening of the hair, better hair gloss, healthier hair, improved body and improved shine.

These results have been observed by persons who have used the composition of the invention. The experimental treatment of persons has been over a period of several years, but there have been no sales of the composition more than year prior to the filing date of this application. The early uses of this composition have all been experimental and no charges were made for these treatments.

The composition of this invention is not to be limitd by the above-described embodiments, and it may be modified in various ways without departing from the spirit of this invention. For instance, the percentages of the various ingredients may be changed from those set forth in the process for making the mixture without departing from the spirit of this invention. Different quantities of the ingredient may be used, but if the ratios are the same, they shall be considered to be within the scope of the claims.

What is claimed:

1. A composition for the treatment of the scalp comprising: mineral oil, a mineral oil soluble extract of ground avocado seeds, and tincture of arnica in liquid form.

2. The composition of claim 1 further including flowers of sulfur, castor oil, cod liver oil, peppermint spirits, orange water, and camphor.

3. A method for the treatment of hair loss in a patient undergoing treatment for angina or radiation therapy for cancer comprising applying to the scalp of said patient an effective amount of the composition set forth in claim 1.

4. A method for the treatment of hair loss in a patient undergoing treatment for angina or radiation therapy for cancer comprising applying to the scalp of said patient an effective amount of the composition set forth in claim 2.

* * * * *